(12) United States Patent
Agnew

(10) Patent No.: US 9,839,539 B2
(45) Date of Patent: Dec. 12, 2017

(54) BOW STENT

(71) Applicant: Cook Medical Technologies LLC, Bloomington, IN (US)

(72) Inventor: Charles W. Agnew, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 358 days.

(21) Appl. No.: 14/639,356

(22) Filed: Mar. 5, 2015

(65) Prior Publication Data

US 2016/0256297 A1  Sep. 8, 2016

(51) Int. Cl.
| | | |
|---|---|---|
| *A61F 2/06* | (2013.01) | |
| *A61F 2/86* | (2013.01) | |
| *A61F 2/966* | (2013.01) | |
| *A61F 2/95* | (2013.01) | |
| *A61F 2/04* | (2013.01) | |

(52) U.S. Cl.
CPC ............... *A61F 2/86* (2013.01); *A61F 2/966* (2013.01); *A61F 2002/044* (2013.01); *A61F 2002/9505* (2013.01); *A61F 2002/9528* (2013.01); *A61F 2002/9665* (2013.01); *A61F 2230/0034* (2013.01); *A61F 2250/0059* (2013.01); *A61F 2250/0096* (2013.01)

(58) Field of Classification Search
CPC .... A61F 2/86; A61F 2/966; A61F 2002/8665; A61F 2002/9505; A61F 2/01; A61F 2002/016; A61F 2/0031; A61F 2/0036; A61F 2/0045; A61B 17/3207; A61B 17/320725; A61B 2017/320791; A61B 2017/320741; A61M 29/00
See application file for complete search history.

(56) References Cited

U.S. PATENT DOCUMENTS

| | | |
|---|---|---|
| 5,195,984 A | 3/1993 | Schatz |
| 5,938,695 A | 8/1999 | Borghi |
| 6,014,589 A | 1/2000 | Farley et al. |
| 6,083,258 A | 7/2000 | Yadav |
| 6,527,800 B1 | 3/2003 | McGuckin, Jr. et al. |
| 6,530,949 B2 | 3/2003 | Konya et al. |
| 6,830,638 B2 | 12/2004 | Boylan et al. |
| 7,582,109 B2 | 9/2009 | DeLegge et al. |

(Continued)

FOREIGN PATENT DOCUMENTS

WO  WO-2009-108942 A1  9/2009

OTHER PUBLICATIONS

Written Opinion and International Search Report issued in corresponding application PCT/US2016/018221, dated Apr. 19, 2016, 11 pgs.

*Primary Examiner* — Jonathan Miles
(74) *Attorney, Agent, or Firm* — Brinks Gilson & Lione

(57) ABSTRACT

A stent having a main linear strut and at least two secondary struts. The main linear strut includes an outer member and an inner member. A distal end of one secondary strut may be attached to a distal end of the inner member. A proximal end of a secondary strut may be attached to a proximal end of the outer member. The ends of the secondary struts that are not attached to the inner and outer member may be joined. Methods of delivering such a stent and collapsing and withdrawing such a stent are also disclosed.

20 Claims, 4 Drawing Sheets

(56) References Cited

U.S. PATENT DOCUMENTS

| | | | |
|---|---|---|---|
| 2004/0204738 A1* | 10/2004 | Weber | A61B 17/22031 |
| | | | 606/200 |
| 2005/0113862 A1 | 5/2005 | Besselink et al. | |
| 2005/0273158 A1 | 12/2005 | Rioux et al. | |
| 2007/0005093 A1* | 1/2007 | Cox | A61B 17/320016 |
| | | | 606/198 |
| 2007/0276467 A1 | 11/2007 | Kalmann | |
| 2009/0018569 A1 | 1/2009 | Desai et al. | |
| 2010/0217381 A1 | 8/2010 | Paul et al. | |
| 2013/0116500 A1* | 5/2013 | Kohl | A61B 17/22 |
| | | | 600/36 |

* cited by examiner

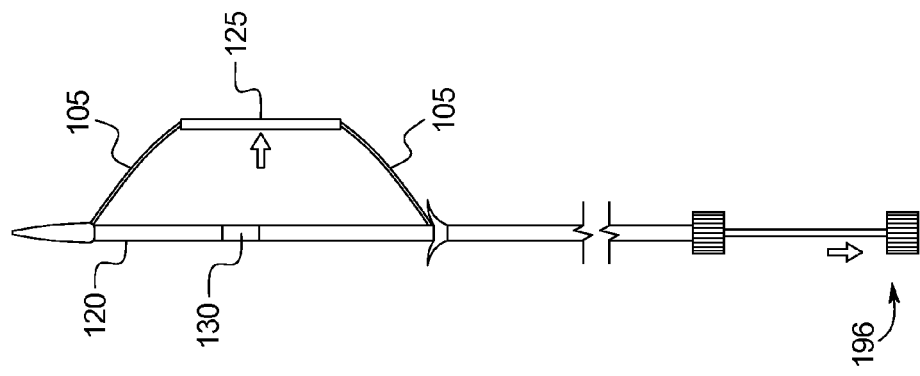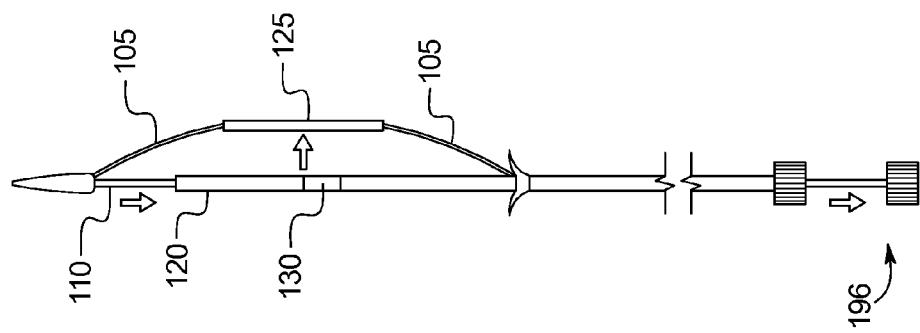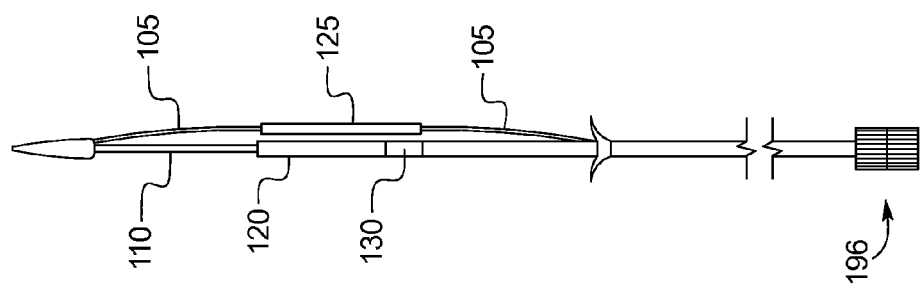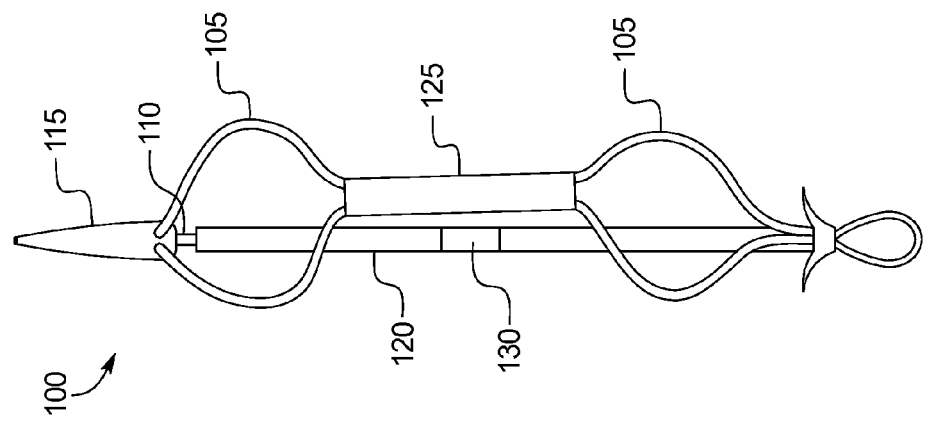

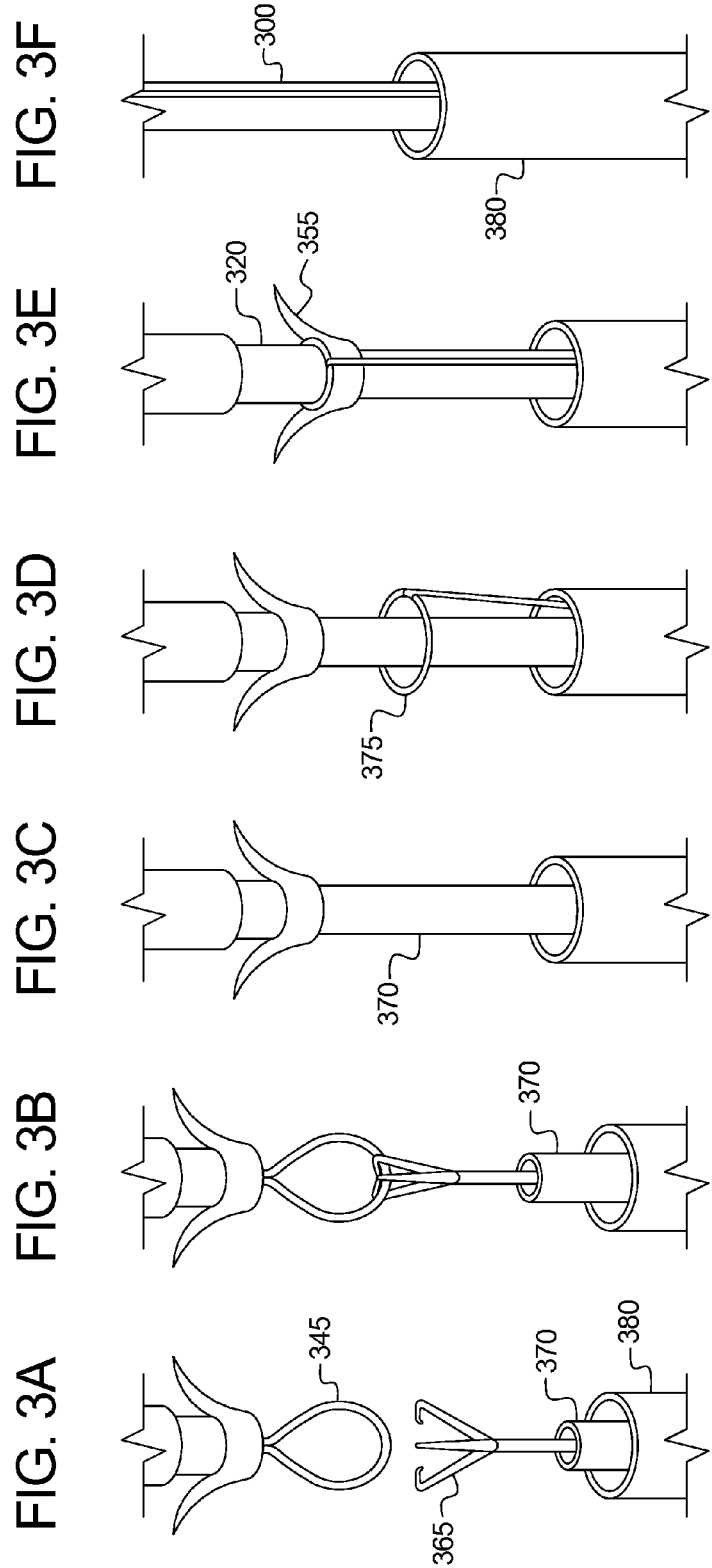

BOW STENT

BACKGROUND

1. Field of the Invention

The present disclosure generally relates to intraluminal support devices. More particularly, the present invention relates to stents having a bow-shaped configuration when expanded.

2. Description of the Related Art

Various types of disease conditions present clinical situations in which a vessel of a patient needs to be artificially supported to maintain an open passageway through which fluids, such as blood, can flow. For example, blood flow through an artery can be impeded due to a build-up of cholesterol on the interior wall of the vessel. Also, vessel walls can be weakened be a variety of conditions, such as aneurysms.

Intraluminal support frames, sometimes referred to as stents, provide an artificial mechanism to support a body vessel. Stents are typically tubular-shaped members that are placed in the lumen of the vessel and, once deployed, exert a radially-outward directed force onto the vessel wall to provide the desired support.

Stents are typically positioned at the point of treatment by navigation through the vessel, and possibly other connected vessels, until the point of treatment is reached. This navigation requires the stent to be able to move axially through the vessel(s) prior to deployment, while still maintaining the ability to exert an outward force on the interior wall once deployed. Accordingly, stents typically have radially collapsed and expanded states. In the collapsed state, the stent has a relatively small diameter that allows it to move axially through the vessel. In the expanded state, the stent has a relatively large diameter that allows it to exert an outward force on the interior wall of the lumen, thereby providing the desired support to the vessel.

Tubular plastic drainage stents, such as biliary stents, pancreatic stents, ureteral stents, etc., are prone to become occluded after only a few months of use, requiring a second procedure to have the old stent replaced. Metal expandable stents offer a wider lumen and are less prone to occlusion over time. However, such stents are difficult to remove and only indicated for palliative treatment end-stage cancer affecting the duct (at least for GI use).

Therefore, a need exists for an expandable and readily removable stent that can also treat benign strictures. A stent that may remain within the patient for six months or more without requiring replacement due to occlusion is also needed.

BRIEF SUMMARY

The present disclosure relates to stents, methods of implanting stents into a lumen of a body, methods of collapsing stents in the lumen, and methods of withdrawing stents from the body.

In one embodiment, the present disclosure relates to a stent comprising a main linear strut, which comprises an outer member and an inner member slidably disposed within a lumen of the outer member. The stent also comprises a first secondary strut having a proximal end and a distal end, the distal end attached to a distal end of the inner member, and a second secondary strut having a proximal end and a distal end, the proximal end attached to a proximal end of the outer member. The proximal end of the first secondary strut is joined to the distal end of the second secondary strut. Additionally, the stent comprises a first coupling element attached to a proximal end of the inner member and a second coupling element attached to the first coupling element, wherein a proximal end of the second coupling element is attached to a handle and the second coupling element is disposed within the outer member.

In another embodiment, a method of delivering the aforementioned stent to a target site in a body is provided. The method comprises positioning the stent in a lumen, retracting the handle such that the second coupling element, first coupling element, and inner member are proximally withdrawn while the outer member remains stationary, shortening a length of the main linear strut thereby causing the first and second secondary struts to bow outward and apply radial force against a wall of the lumen.

In an additional embodiment, a method of withdrawing the aforementioned stent is provided. The method comprises advancing a retrieval device to the stent at the target site, securing the first coupling element with the retrieval device, and proximally retracting the retrieval device, thereby proximally withdrawing the stent from the target site.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention follows hereafter with specific reference being made to the drawings in which:

FIG. 1A shows a stent of the present disclosure in its expanded configuration;

FIG. 1B shows a stent of the present disclosure in its collapsed configuration;

FIG. 1C shows a stent of the present disclosure in a partially expanded configuration;

FIG. 1D shows a stent of the present disclosure in its expanded configuration;

FIGS. 3A-3F show a step-wise method for retrieving a stent;

DETAILED DESCRIPTION

Figure 2A:
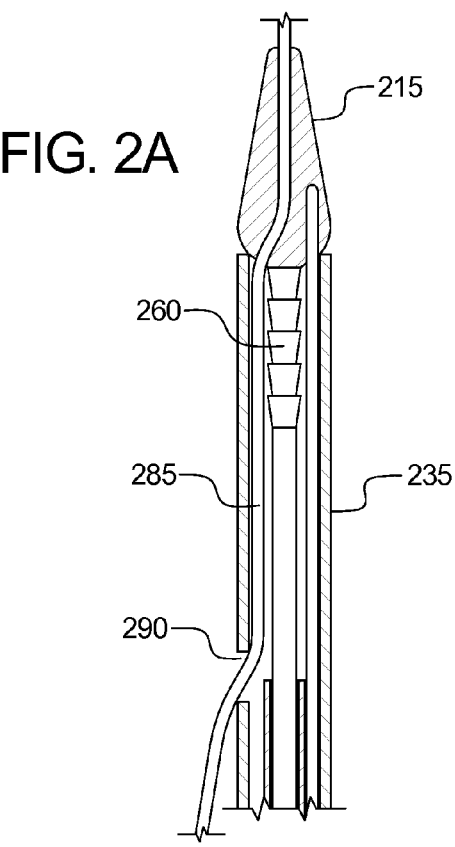
FIG. 2A shows a distal end of a stent according to one embodiment of the present disclosure.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as conventional fabrication and assembly.

In the present application, the terms "proximal" and "distal" are used to describe the opposing axial ends of particular components of the medical devices disclosed herein, including the various components of the stents described herein. The term "proximal" is used in its conventional sense to refer to the end of an apparatus (or component thereof) that is closest to the operator or medical professional during use of the apparatus. The term "distal" is used in its conventional sense to refer to the end of the apparatus (or component thereof) that is initially inserted into the body of the patient, or that is furthest from the operator or medical professional using the device.

In some embodiments, the present disclosure relates to a stent comprising a main linear strut having an adjustable length. When the stent is placed or implanted in a duct or passageway in the body, it can be manipulated to increase or decrease the length of the main strut. When decreasing the length of the main strut, one or more adjacent secondary struts attached to the main strut are caused to bow outward such that radial force is applied toward the wall opposite the main strut, thereby opening the stricture and maintaining patency of the passageway. The presently disclosed stent may be used to enlarge a sphincter or any passageway, such as a passageway containing a stricture or a passageway that needs to be enlarged to allow passage of a stone.

In FIG. 1A, a bow stent (100) is generally depicted having two secondary struts (105) attached at a distal end and a proximal end of the main strut. The main strut comprises an inner coaxial member (110) and an outer coaxial member (120). In some embodiments, each secondary strut (105) comprises a loop formation and a pair of legs, which are attached to the main strut. In such embodiments, the secondary struts may be attached or joined to each other in an end-to-end fashion and in certain aspects, the point of attachment or joinder is covered by a strip of material (125). At the distal end of the bow stent (100), an end of a secondary strut (105) may be attached, bonded, or otherwise adhered to a distal end of the inner coaxial member (110) or it may be attached, bonded or otherwise adhered to a proximal end of a tip (115), which may be attached, bonded, or otherwise adhered to the distal end of the inner member (110). Further, an end of a secondary strut (105) may be attached, bonded, or otherwise adhered to a proximal end of the outer member (120).

In other embodiments, each secondary strut may comprise a proximal and distal end and the secondary struts may be placed side-by-side along the length of the main strut. At the distal end of the bow stent (100), an end of a first secondary strut and a second secondary strut may be attached, bonded, or otherwise adhered to a distal end of the inner coaxial member (110) or the ends may be attached, bonded or otherwise adhered to a proximal end of a tip (115), which may be attached, bonded, or otherwise adhered to the distal end of the inner member (110). Further, the other end of the first secondary strut and the other end of the second secondary strut may be attached, bonded, or otherwise adhered to a proximal end of the outer member (120). A strip of material (125) may be disposed around a midsection of each strut, thereby joining together the side-by-side secondary struts.

When implanted into a passageway, the secondary struts (105) follow obliquely and circumferentially along the wall of the passageway. In some embodiments, the secondary struts (105) are connected to one another by a strip of material (125) located approximately 180° in relation to the main strut. The strip of material (125), which provides for a broader surface area to apply against the wall of the stricture, may comprise a thin polymeric material, for example. In some embodiments, the strip of material (125) may comprise any plastic or polymer, such as polyurethane, or any other material, such as a fabric, that allows for the secondary struts (105) to apply force against the wall of the passageway to maintain patency. The strip of material (125) may also comprise any combination of these materials. The use of a thin film material permits the stent to be readily collapsed inside of a delivery system, such as an endoscopic delivery system. The strip of material (125) may be fairly narrow or it may be wider to provide greater separation of the secondary struts (105) (e.g., up to about 120° apart) to more equally distribute the stent's outward radial force about the circumference of the passageway. The width of the strip of material (125) can be chosen by one of ordinary skill in the art depending upon the target location of the bow stent. In some embodiments, the width may be from about 1 mm to about 10 mm. The secondary struts (105) may be attached, bonded, or otherwise adhered to the strip of material (125). In some embodiments, the secondary struts (105) may be embedded within the material (125) to ensure adequate radial force.

In some embodiments, the outer member (120) of the main strut may comprise a marker (130). The marker (130) may be, for example, fluoroscopically or echogenically imageable. As such, the marker (130) can help position the stent (100) at the target location while the outer member (120) is held stationary and the inner member (110) is withdrawn. As will be described more fully below, when the inner member (110) is withdrawn, the center of the "bow" (e.g. the strip of material (125)) expands and moves into alignment with the marker (130).

While certain embodiments described above use a strip of material (125) to connect the secondary struts (105), other embodiments contemplate using, for example, interconnecting struts between the two secondary struts (105) or welding of the ends of the secondary struts (105) to join them together. In other embodiments, the ends of the secondary struts may simply be connected and the strip of material (125) may be absent. For example, with respect to FIG. 1A, if the strip of material (125) were removed, one embodiment comprises two parallel wires connecting the secondary struts (105). The wires need not be parallel and in some embodiments the wires may be twisted or woven around each other in a spiral configuration. In a further embodiment, the stent (100) may be laser cut or molded from plastic to form the desired stent/strut configuration.

Delivery of the stent into a passageway or lumen of a patient may be accomplished using any delivery systems known in the art. In some embodiments, such as those depicted in FIGS. 2A and 2B, the stent is delivered within an outer sheath (235) and in other embodiments, the stent may be delivered unsheathed over an inner delivery member. In FIG. 2C, which is an exploded view of a stent and delivery system, a second coupling element (240) is attached to a first coupling element (245) that extends proximally from the coaxial inner member (210) inside of the coaxial outer member (220). The first and second coupling elements are not particularly limited and can be any complimentary interlocking structures. For example, in the drawing figures, the first coupling element is shown as a capture loop and the second coupling element is shown as a tether. However, the first and second coupling elements are not limited to capture loops and tethers and in other embodiments, the first and second coupling elements may comprise balls, hooks, or any other complimentary interlocking structures.

In embodiments using a sheath (235), as the stent is unsheathed and advanced into the duct, a pusher member (250), having a passageway through which tether (240) is fed, is used to urge the stent into the duct while using the marker (230) on the main strut to guide the stent to the target location (stricture). It should be noted that in FIG. 2C, secondary struts (205) are shown as cut off but this is merely to simplify the drawing figure and in all embodiments, the stent comprises the secondary struts.

Figure 6:
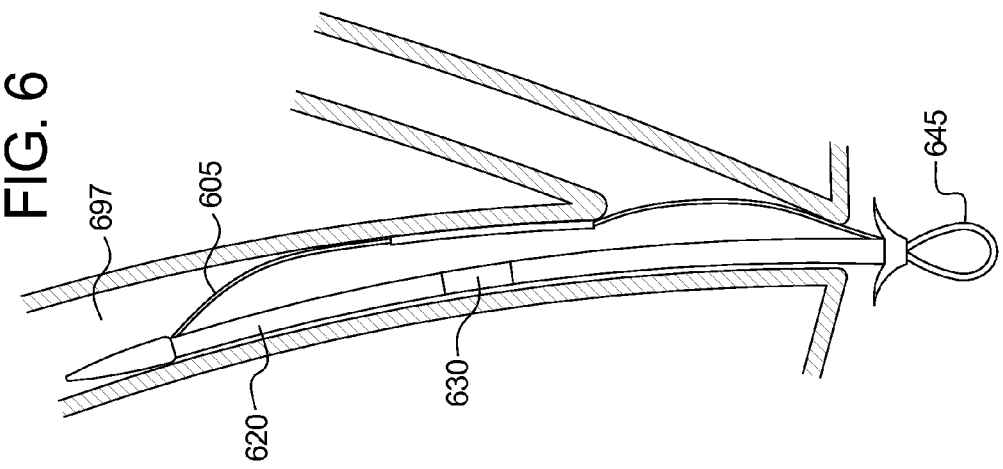
FIG. 6 shows a stent implanted in a lumen of a body of a patient.

The proximal end of the outer coaxial member (220) may comprise one or more retention flaps (255) which, during delivery, may remain outside of the duct to prevent ingress of the stent into the duct. The retention flap(s) (255) may also create and maintain the opening at the sphincter into the duodenum if the stent is being used endoscopically. When the stent has been positioned at the target location, the tether (240) is retracted via a proximal handle (see 196 in FIGS. 1B-1D) so that the attached capture loop (245) and inner member (210) are caused to move proximally relative to the stationary outer member (220). During retraction, the length of the main strut is shortened and the secondary struts (205) bow outward and apply radial force against the wall of the target stricture. In some embodiments, such as depicted in FIG. 6, the main strut comprises sufficient rigidity such that it does not bow and/or is substantially inflexible. As can be seen in FIG. 6, in some embodiments, the entire length of the main strut contacts the wall of the duct (697) when implanted therein.

Certain aspects of a method of delivering a stent are depicted in FIGS. 1B-1D. FIG. 1B depicts the stent in an unexpanded configuration, which it may have when it arrives at the target location. By retracting the handle (196), the secondary struts (105) begin to bow outward, as in FIG. 1C. Additionally, the inner member (110) begins to slide within the outer member (120). When the handle (196) is retracted even further, as in FIG. 1D, the secondary struts (105) bow further outward until they contact and sufficiently open the duct. The inner member (110) also completely or substantially completely slides within the outer member (120). Locking members (not shown—but further explained in connection with FIG. 2A) near the distal ends of the inner (110) and outer (120) members engage and lock the stent in the expanded configuration.

Figure 2C:
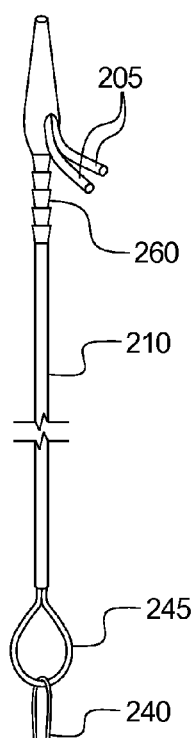
FIG. 2C shows an exploded view of a stent according to an embodiment of the present disclosure.
Figure 2B:
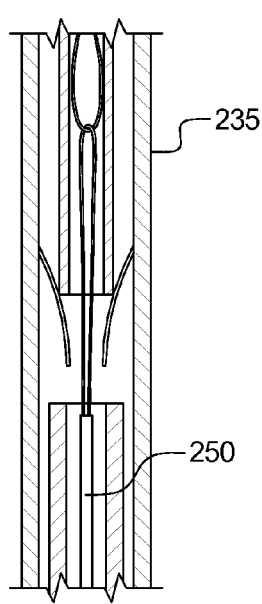
FIG. 2B shows a proximal end of a stent according to one embodiment of the present disclosure.

With reference to FIGS. 2A and 2C, as the stent attains its fully expanded diameter, complimentary structures/locking members (260) on the outer wall of inner member (210) and on the inner wall of outer member (not shown) of the main strut engage to lock the stent into position with the inner member (210) substantially or completely inside of the outer member (220). In some embodiments, the locking members (260) are located near the distal end of the inner member (210) and near the distal end of the outer member (220). Optionally, a separate locking element or mechanism (not shown) may be advanced or otherwise deployed to prevent the inner member from sliding and collapsing the bowed stent. The tether (240) may then be cut or unsecured from the capture loop (245) so that it can be withdrawn from the patient, leaving the capture loop (245) extending proximally out of the outer member (220) and extending, for example, into the duodenum if the stent is being used endoscopically (see, for example, reference numeral 645 in FIG. 6).

Various techniques may be used to collapse and remove the stent from the body. One illustrative technique is outlined in FIGS. 3A-3F. This technique comprises advancing a retrieval system endoscopically or using a steerable catheter (guided fluoroscopically or under ultrasound). Specifically, a retrieval device (365) may be advanced to secure the capture loop (345), which is preferably enhanced for visibility under imaging. Although the retrieval device (365) is shown as a hook in the drawings, it is not limited to a hook and may be a snare, forceps, or any other retrieval/capture means. Once the loop (345) is secured by the hook (365), it is drawn with the retrieval device into a catheter (370), which also may function as a pusher to help collapse the stent (e.g. catheter (370) may be distally advanced). A snare (375) or similar securing means may be advanced over the outer member of the main strut and then over the retention flap (355) to capture and secure the proximal end of the outer member (320). Maintaining counter-pressure against the proximal end of the outer member (320), the catheter (370) may be advanced into the lumen of the outer member (320) to urge the inner member to move distally, cause disengagement of the locking members, and allow the main strut to elongate to its pre-deployment configuration, thereby collapsing the stent. As the retrieval system is withdrawn, the stent (300) is pulled back from the duct. An optional outer sheath (380) may be used to re-sheath the stent (300) for withdrawal into the scope and/or removal from the patient.

Since the presently disclosed stent is collapsible and comprises struts that primarily extend in general alignment with the passageway, it is much easier to remove than traditional expandable stents where tissue growth over and between the struts can be problematic. The limited amount of stent material covering the wall advantageously preserves the endothelial surface, which makes occlusion by bacterial growth or accumulation of substances in the bile, urine, etc., less likely. In some embodiments, the stent is expandable and in other embodiments, the stent is self-expanding. The self-expanding stent may comprise materials such nitinol or other shape memory materials, to achieve adequate expansion and radial force.

In some embodiments, the main and secondary struts comprise polymeric or other synthetic materials having sufficient flexibility and rigidity. In certain embodiments, the outer member of the main strut may comprise a small diameter, such as about 0.1 mm to about 10 mm or about 0.1 mm to about 4 mm, or any sub-range thereof, braided or coiled reinforced polymer tube (e.g. Flexor® tubing), multifilar wire tubing, EUSN-type coil, and the like, that is preferably stiffer than the secondary struts (at least once the inner member is disposed within the outer member) so that the secondary struts bow more readily and the main strut is pushed against the opposite wall. In some embodiments, the inner member may comprise a solid plastic or metal element that is connected distally to the tip and proximally to the capture loop.

Suitable materials that may be used to manufacture the main strut (inner and outer members) and the secondary struts of the bow stent include, but are not limited to, biocompatible materials. The materials may include stainless steel, nickel, silver, platinum, palladium, gold, titanium, tantalum, iridium, tungsten, cobalt, chromium, a nickel-titanium alloy, a superelastic nickel-titanium (NiTi) alloy sold under the trade name NITINOL® or inconel. Examples of other materials that may be used to form the various components of the bow stent include carbon or carbon fiber, cellulose acetate, cellulose nitrate, silicone, polyethylene terephthalate, polyurethane, polyamide, polyester, polyorthoester, polyanhydride, polyether sulfone, polycarbonate, polypropylene, ultra-high molecular weight polyethylene, polytetrafluoroethylene, or another biocompatible polymeric material, polylactic acid, polyglycolic acid or copolymers thereof, a polyanhydride, polycaprolactone, polyhydroxybutyrate valerate or another biodegradable polymer, or mixtures or copolymers of any combination of these materials.

In certain embodiments, such as depicted in FIG. 2A, the device may be backloaded over a guide wire (285) with the guide wire (285) exiting at the proximal end of the tip (215). The guide wire (285) then extends alongside the stent within the outer delivery sheath (235), if present, before exiting the sheath via a side port (290) (e.g., about 5-10 cm from the distal end of the device).

Figure 4A:
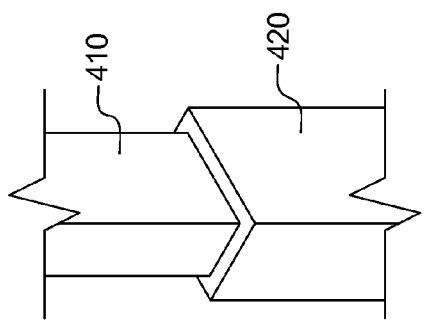
FIGS. 4A-4B show alternate embodiments of an inner member and outer member of a main strut.
Figure 4B:
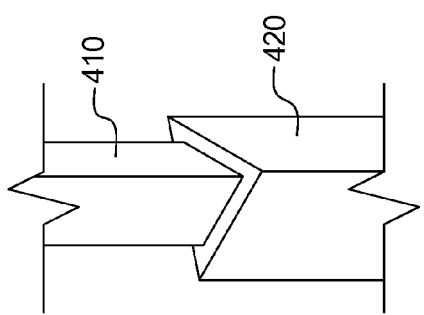

While the inner and outer members of the stent are depicted as coaxial tubular members, they may have other complimentary shapes, such as those depicted in FIGS. 4A and 4B. In FIG. 4A, the inner (410) and outer (420) members are flat or flattened to lower the profile of the stent. In FIG. 4B, the inner (410) and outer (420) members are triangular shaped, which helps the stent to resist bending. Additionally, the inner and outer members may slide relative to one another in a channel or track arrangement, which allows for one member to slide relative to the other.

Figure 5:
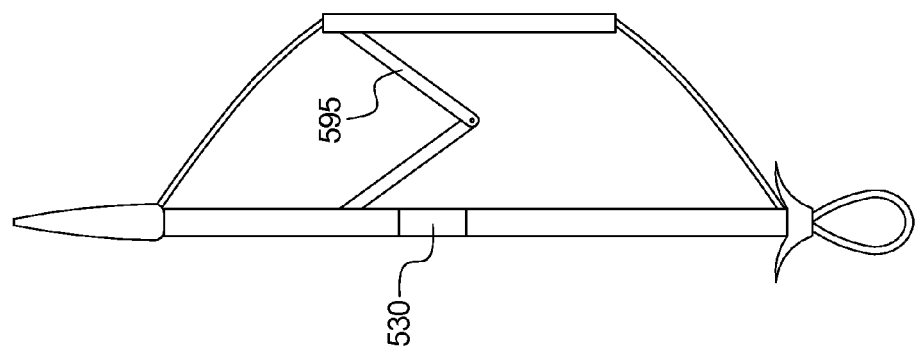
FIG. 5 shows an alternate embodiment of a stent according to the present disclosure.

FIG. 5 shows an alternate embodiment of the presently disclosed stent having one or more auxiliary serpentine struts (595) positioned midway along the main strut to provide additional radial force at the target zone, and to provide a countering force against the main strut to prevent it from bowing away from the duct wall. In some embodiments, the auxiliary struts (595) are each attached to the outer member or the marker (530), which may comprise a metal, on the outer member of the main strut. The auxiliary struts (595) may be configured to expand and collapse with the rest of the stent and may be covered with any biocompatible material to prevent tissue ingrowth. Although FIG. 5 depicts a single-bend auxiliary strut (595), the stent may comprise more than one auxiliary strut and/or the strut may include additional bends.

All of the devices and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a retention flap" is intended to include "at least one retention flap" or "one or more retention flaps."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A stent comprising:
   a primary strut, which comprises a first primary strut member and a second primary strut member longitudinally slidably attached to the first primary strut member;
   wherein the first primary strut member comprises a proximal end and a distal end;
   wherein the second primary strut member comprises a proximal end, a distal end, and a collar mounted between the proximal end and the distal end; and
   wherein the proximal end of the second primary strut member defines the proximal end of the primary strut;
   a first length defined by the distance between the distal end of the first primary strut member and the collar of the second primary strut member;
   a second length defined by the distance between the proximal end of the second primary strut member and the collar of the second primary strut member; and
   a first secondary strut having a proximal end and a distal end, the distal end of the first secondary strut attached near the distal end of the first primary strut member and the proximal end of the first secondary strut attached at the collar of the second primary strut member;
   configured wherein the first primary strut member and the second primary strut member are slidably attached together in a manner such that movement of one of the first primary strut member and the second primary strut member relative to the other bows at least one portion of the first secondary strut away from the primary strut by shortening the first length while the second length remains unchanged.

2. The stent of claim 1, where the first primary strut member is configured as an inner member and at least partially coaxially slidably disposed in a lumen of the second primary strut member, which is configured as an outer member.

3. The stent of claim 1, further comprising a second secondary strut, wherein the first secondary strut has two first secondary strut ends, and the second secondary strut has two second secondary strut ends, and wherein
   both first secondary strut ends are attached to the primary strut near a distal end of the primary strut and both second secondary strut ends are attached to the primary strut near the collar.

4. The stent of claim 3, wherein a strip of material surrounds and joins a portion of the first secondary strut with a portion of the second secondary strut.

5. The stent of claim 1, comprising a self-expanding construction that is configured with one or more shape memory materials providing adequate expansion and radial force to effect the bow of at least one portion of the first secondary strut away from the primary strut.

6. The stent of claim 1, further comprising a handle, wherein a pusher member is disposed between the proximal end of the first primary strut member and a distal end of the handle.

7. The stent of claim 1, wherein the primary strut comprises one or more locking members.

8. The stent of claim 1, further comprising an outer sheath, with the stent being slidably disposed within the outer sheath.

9. The stent of claim 8, wherein the sheath includes a guide wire lumen for wire-guided introduction of the sheath.

10. The stent of claim 1, wherein the primary strut comprises one or more auxiliary struts.

11. A method of delivering a stent, comprising:
providing the stent of claim 1;
positioning the stent in a lumen;
actuating one or both of the first primary strut member and the second primary strut member in a manner shortening a longitudinal length of the primary strut thereby causing at least the first secondary strut to bow outward and apply radial force against a wall of the lumen.

12. The method of claim 11, wherein an entire length of the primary strut contacts the wall of the lumen.

13. The method of claim 11, wherein the second primary strut member slides within the first primary strut member upon retracting a handle that is in mechanical communication with one of first primary strut member and the second primary strut member.

14. The method of claim 13, wherein an outer surface of the distal end of the second primary strut member comprises one or more locking members and an inner surface of a distal end of the lumen of the first primary strut member comprises one or more locking members, further wherein when the second primary strut member slides within the first primary strut member, the one or more locking members of the second primary strut member engage the one or more locking members of the first primary strut member, thereby locking the stent in an expanded configuration.

15. The method of claim 11, where the step of positioning the stent in a lumen includes operating a delivery system, which delivery system comprises a first coupling element and a second coupling element releasably coupled together, further comprising—after the actuating step—a step of uncoupling the second coupling element from the first coupling element.

16. The method of claim 15, further comprising withdrawing the second coupling element from the body.

17. The method of claim 16, wherein the first coupling element extends proximally from the first primary strut member.

18. The method of claim 17, further comprising:
advancing a retrieval device to a proximal end of the stent;
securing the first coupling element with the retrieval device;
proximally retracting the retrieval device, thereby proximally withdrawing the stent from the target site.

19. The method of claim 18, wherein the retrieval device extends distally from within a pusher member, further wherein the pusher member is distally advanced into the lumen of the first primary strut member before proximally withdrawing the stent.

20. The method of claim 19, wherein the pusher member urges the second primary strut member to move distally, thereby disengaging the one or more locking members of the inner and first primary strut members before proximally withdrawing the stent.

* * * * *